US009931304B2

(12) United States Patent
Staniforth et al.

(10) Patent No.: US 9,931,304 B2
(45) **Date of Patent: *Apr. 3, 2018**

(54) METHOD OF MAKING PARTICLES FOR USE IN A PHARMACEUTICAL COMPOSITION

(71) Applicant: VECTURA LIMITED, Wiltshire (GB)

(72) Inventors: John Nicholas Staniforth, Wiltshire (GB); Matthew Michael Green, Wiltshire (GB); David Alexander Vodden Morton, Wiltshire (GB)

(73) Assignee: VECTURA LIMITED, Chippenham (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/553,187

(22) Filed: Nov. 25, 2014

(65) Prior Publication Data

US 2015/0079185 A1 Mar. 19, 2015

Related U.S. Application Data

(63) Continuation of application No. 13/623,326, filed on Sep. 20, 2012, now Pat. No. 8,956,661, which is a continuation of application No. 12/767,530, filed on Apr. 26, 2010, now Pat. No. 8,303,991, which is a continuation-in-part of application No. 10/433,072, filed as application No. PCT/GB01/05315 on Nov. 30, 2001, now Pat. No. 7,736,670.

(30) Foreign Application Priority Data

| | | |
|---|---|---|
| Nov. 30, 2000 | (GB) | 0029261.5 |
| Dec. 19, 2000 | (GB) | 0030946.8 |
| Apr. 9, 2001 | (WO) | PCT/GB01/01606 |
| Oct. 5, 2001 | (GB) | 0124010.0 |

(51) Int. Cl.

| | |
|---|---|
| *A61K 9/16* | (2006.01) |
| *A61K 9/50* | (2006.01) |
| *A61K 9/51* | (2006.01) |
| *A61K 9/00* | (2006.01) |
| *A61K 9/14* | (2006.01) |
| *A61K 31/137* | (2006.01) |
| *A61K 47/06* | (2006.01) |
| *A61K 47/10* | (2017.01) |
| *A61K 47/12* | (2006.01) |
| *A61K 47/32* | (2006.01) |

(52) U.S. Cl.
CPC ............ *A61K 9/5115* (2013.01); *A61K 9/008* (2013.01); *A61K 9/0075* (2013.01); *A61K 9/145* (2013.01); *A61K 9/167* (2013.01); *A61K 9/1617* (2013.01); *A61K 9/50* (2013.01); *A61K 9/5089* (2013.01); *A61K 31/137* (2013.01); *A61K 47/06* (2013.01); *A61K 47/10* (2013.01); *A61K 47/12* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 4,906,476 A | | 3/1990 | Radhakrishnan | |
| 5,145,684 A | | 9/1992 | Liversidge et al. | |
| 5,188,837 A | | 2/1993 | Domb | |
| 5,190,764 A | | 3/1993 | Chiba et al. | |
| 5,192,528 A | | 3/1993 | Radhakrishnan | |
| 5,223,244 A | | 6/1993 | Moro et al. | |
| 5,320,906 A | | 6/1994 | Eley et al. | |
| 5,376,386 A | | 12/1994 | Ganderton et al. | |
| 5,413,804 A | | 5/1995 | Rhodes et al. | |
| 5,441,753 A | * | 8/1995 | McGinley | A21D 2/188 426/103 |
| 5,478,578 A | | 12/1995 | Arnold et al. | |
| 5,506,203 A | | 4/1996 | Backstrom et al. | |
| 5,612,053 A | | 3/1997 | Baichwal et al. | |
| 5,663,198 A | | 9/1997 | Reul et al. | |
| 5,672,581 A | | 9/1997 | Rubsamen et al. | |
| 5,655,523 A | | 12/1997 | Hodson et al. | |
| 5,738,865 A | | 4/1998 | Baichwal et al. | |
| 5,823,182 A | | 10/1998 | Van Oort | |
| 5,908,639 A | | 6/1999 | Simpkin et al. | |

(Continued)

FOREIGN PATENT DOCUMENTS

| | | |
|---|---|---|
| EP | 1430887 | 6/2004 |
| GB | 1381872 | 1/1975 |
| GB | 0124009.2 | 11/2001 |
| JP | 05301810 | 11/1998 |
| WO | 1996019199 | 6/1986 |
| WO | 1987005213 | 9/1987 |
| WO | 1995000127 | 1/1995 |
| WO | 1996019197 | 6/1996 |
| WO | 1996019198 | 6/1996 |

(Continued)

OTHER PUBLICATIONS

Tanno, Kouichi. "Current status of the mechanofusion process for producing composite particles." KONA Powder and Particle Journal 8.0 (1990): 74-82.*

(Continued)

*Primary Examiner* — Abigail Vanhorn
(74) *Attorney, Agent, or Firm* — Matthew S. Gibson; Reed Smith LLP; Ryan P. Cox

(57) ABSTRACT

The invention relates to a method for making composite active particles for use in a pharmaceutical composition for pulmonary administration, the method comprising a milling step in which particles of active material are milled in the presence of particles of an additive material which is suitable for the promotion of the dispersal of the composite active particles upon actuation of an inhaler. The invention also relates to compositions for inhalation prepared by the method.

14 Claims, 6 Drawing Sheets

(56) References Cited

U.S. PATENT DOCUMENTS

| | | | |
|---|---|---|---|
| 5,918,594 A | 7/1999 | Asking et al. |
| 5,931,809 A | 8/1999 | Gruber et al. |
| 5,935,555 A | 8/1999 | Stutts et al. |
| 5,945,123 A | 8/1999 | Hermelin |
| 5,993,846 A | 11/1999 | Friedman et al. |
| 5,997,848 A | 12/1999 | Patton et al. |
| 6,045,828 A | 4/2000 | Bystrom |
| 6,103,271 A | 8/2000 | Morrison et al. |
| 6,153,224 A | 11/2000 | Staniforth |
| 6,178,414 B1 | 1/2001 | Beckmann et al. |
| 6,221,338 B1 | 4/2001 | Staniforth |
| 6,197,369 B1 | 6/2001 | Watano et al. |
| 6,360,743 B1 | 3/2002 | Andersson et al. |
| 6,404,772 B1 | 6/2002 | Beach et al. |
| 6,475,523 B1 | 11/2002 | Staniforth |
| 6,477,670 B1 | 11/2002 | Ahmadvand |
| 6,521,260 B1 | 2/2003 | Stani Froth |
| 6,528,096 B1 | 3/2003 | Musa et al. |
| 6,645,466 B1 | 11/2003 | Keller et al. |
| 6,780,508 B1 | 8/2004 | Caponetti et al. |
| 6,984,404 B1 | 1/2006 | Talton et al. |
| 7,063,748 B2 | 6/2006 | Talton et al. |
| 7,132,115 B2 | 11/2006 | Musa et al. |
| 7,541,022 B2 | 6/2009 | Staniforth et al. |
| 7,736,670 B2 | 6/2010 | Staniforth et al. |
| 7,744,855 B2 | 6/2010 | Staniforth et al. |
| 8,048,451 B2 | 11/2011 | Staniforth et al. |
| 8,101,160 B2 | 1/2012 | Staniforth et al. |
| 2002/0082304 A1* | 6/2002 | Bess ............... A61K 9/146 514/646 |
| 2003/0118514 A1 | 6/2003 | Larhrib et al. |
| 2003/0162835 A1 | 8/2003 | Staniforth et al. |
| 2003/0165436 A1 | 9/2003 | Staniforth et al. |
| 2003/0175214 A1 | 9/2003 | Staniforth et al. |
| 2003/0185764 A1 | 10/2003 | Staniforth et al. |
| 2004/0047810 A1 | 3/2004 | Staniforth |
| 2004/0071635 A1 | 4/2004 | Staniforth |
| 2005/0152849 A1 | 7/2005 | Staniforth |
| 2006/0147389 A1 | 7/2006 | Staniforth et al. |
| 2006/0257491 A1 | 11/2006 | Morton et al. |
| 2006/0292081 A1 | 12/2006 | Morton |
| 2007/0081948 A1 | 4/2007 | Staniforth et al. |
| 2008/0220078 A1 | 9/2008 | Morton et al. |
| 2011/0139152 A1 | 6/2011 | Morton et al. |
| 2011/0236492 A1 | 9/2011 | Morton |

FOREIGN PATENT DOCUMENTS

| | | |
|---|---|---|
| WO | 1996019199 | 6/1996 |
| WO | 1996023485 | 8/1996 |
| WO | 1997003649 | 2/1997 |
| WO | 1999038493 | 8/1999 |
| WO | 1999053901 | 10/1999 |
| WO | 200028969 | 5/2000 |
| WO | 200028979 | 5/2000 |
| WO | 2000027363 | 5/2000 |
| WO | WO 2000/027363 A1 * | 5/2000 |
| WO | 200033811 | 6/2000 |
| WO | 2000033789 | 6/2000 |
| WO | 2000053157 | 9/2000 |
| WO | 2000053158 | 9/2000 |
| WO | 2001076575 | 10/2001 |
| WO | 0230394 | 4/2002 |
| WO | 2002043700 | 6/2002 |

OTHER PUBLICATIONS

Rowe, Raymond C; Sheskey, Paul J; Quinn, Marian E. (2009). Handbook of Pharmaceutical Excipients. Pharmaceutical Press. Retrieved Jun. 14, 2017, from <http://www.myilibrary.com?ID=231717>.*

Peart J. et al. "Multicomponent Particle Interactions in Dry Powder Aerosols." Pharmaceutical Research, Spring New York LLC, US, vol. 14, No. 11-S, Jan. 1, 1997, pp. S142-S143, XP001030455.

Fuki et al. "Effect of magnesium stearate or calcium stearate as additives on dissolution profiles of diltiazem hydrochloride from press-coated tablets with hydroxypropylmethycellulose acetate succinate in the outer shell." International Journal of Pharmaceutics 216 (2001) 137-146.

Wade et al., "Microcrystalline Cellulose." Handbook of Pharmaceutical Excipients. Second Edition, 1994, pp. 84-90.

Wade et al., "Magnesium Stearate." Handbook of Pharmaceutical Excipients. Second Edition, 1994, pp. 280-282.

Kibbe, "Magnesium Stearate." Handbook of Pharmaceutical Excipients. Third Edition, 2000, pp. 305-308.

Kawashima et al., "Design of inhalation ry powder of pranlukast hydrate to improve dispersibility by the surface modification with light anhydrous silicic acid (AEROSIL 200)." International Journal of Pharmaceutics 173 (1998) 243-251.

Koishi et al., "Preparation and Surface Properties of Encapsulated Powder Pharmaceuticals." Applied Biochemistry and Biotechnology, vol. 10, 1984, pp. 259-262.

International Search Report of International Application No. PCT/GB01/05305 (5 Pages) (Jul. 18, 2002).

Preparation for Inhalation; Aerodynamic Assessment of Fine Particles—Fine Particle Dose and Particle Size Distribution. Euopean Pharmacopeia (Supplement 2000): Sec. 2.9.18.

William C. Hinds; "Aerosol Technology, Properties, Behavior and Measurement of Airborne Particles; Second Edition." John Wiley & Sons, Inc. (1999); pp. 51-52 and 402-408.

G.W. Hallworth et al.; "The Twin Impinger; A Simple Device for Assessing the Delivery of Drugs From Metered Dose Pressurized Aerosol Inhalers." J. Pharm. Pharmacol., vol. 39 (1987); pp. 966-972.

I. Colbeck; "Physical and Chemical Properties of Aerosols." Blackie Academic & Professional (Dec. 31, 1997); pp. 18-20.

Merriam-Webster Incorporated: Springfield, Massachussetts, 1993, pp. 311.

Naito et al., The Iron Steel Institute of Japan International, 1993, 33(9), pp. 915-924.

Kawashima, et al; 'Design of Inhalation Dry Powder of Pranlukast Hydrate to Improve Dispersibility by the Surgace Modication With Light Anhydrous Silicic Acid (Aerosol 200). International Journal of Pharmaceutics 173 (1998) pp. 243-251.

Aulton; "Pharmaceutics: The Science of Dosage Form Design." Pharmaceutical Technology, (1998) pp. 584-591.

Hamada, K. "The Surface Modiciation of Solida Particle by Adhesion of Liquid Using Hybridizer." Funtai Kaishi, 1998, 35(6), pp. 447-450.

Merriam-Webster's Collegiate Dictionary, 10th Ed., Merriam-Wester, Inc.,: Springfield, Massachussetts. 1995, pp. 739.

Fu et al., "Self-Assembly Bilayer Molecular Coating on Magnetic Nanoparticles." Applied Surface Science. 2001. 181:173-178.

International Search Report, dated Jul. 15, 2002, Issued in Connection With Corresponding International Publication WO 02/43701.

Pillai et al. 1998 "Controlled dissolution from wax-coated aerosol particles in canine lungs" J. Appl. Physiol 84:717-725.

Koishi et al. 1984 "Preparation and Surface Properties of Encapsulated Powder Pharmaceuticals" Applied Biochemistry and Biotechnology 10:259-263.

Koishi and Ishizanka 1988 "Mechanochemical encapsulation process by dry blending." In: Hsieh, S.T. (ed.) Controlled Release Systems: Fabrication Technology, (1988) vol. 1, CRC Press, Florida, 109-142.

"Magnesium Stearate", Handbook of Pharmaceutical Excipients, Am. Pharm. Ass'n, 2d Ed., pp. 280-282 (1994).

"Magnesium Stearate", Handbook of Pharmaceutical Excipients, Am. Pharm. Ass'n, 3d Ed., p. 305-308 (2000).

Terzano and Colombo 1999 "State of the art and new perspectives on dry powder inhalation" European Review for Medical and Pharmacological Sciences 3:247-254.

Talton et al. 2000 "Nano-Thin Coatings for Improved Lung Targeting of Glucocorticoid Dry Powders" Respiratory Drug Delivery VII:67-74.

Gupta and Hickey 1991 "Contemporary approaches in aerosolized drug delivery to the lung" J Control Release 17:129-148.

(56) References Cited

OTHER PUBLICATIONS

Hochhaus et al. 1997 "Pharmacokinetic/pharmacodynamic aspects of aerosol therapy using glucocorticoids as a model" J Clin Pharmacol 37:881-892.
Hickey et al. 1990 "Effect of hydrophobic coating on the behavior of a hygroscopic aerosol powder in an environment of controlled temperature and relative humidity" J Pharm Sci 79(11):1009-1014.
Talton 1999 Dissertation "Pulmonary Targeting of Inhaled Glucocorticoid Dry Powders".
Pfeffer et al. 2001 "Synthesis of engineered particulates with tailored properties using dry particle coating" Powder Technology 117:40-67.
Mizota et al. 1991 "Microstructure and adhesion mechanism of mechanically prepared composite particles" Materials Science and Engineering B10:139-147.
Ata et al. 1998 "Magnetically Assisted Impaction Coating Process to Synthesize Engineered Particulates With Controlled Surface Characteristics" Mat. Res. Soc. Symp. Proc. 501 333-338.
Singh et al. 1997 "Dry Coating Method for Surface Modification of Particulates" Surface Modification Technologies X 909-917.
Kaye, B.H. 1997 "Powder Mixing".
Koishi et al. 1987 "Dry impact blending preparation and properties of encapsulated powder nylon 12" Chimica oggi luglio-agosto 43-45.
Honda et al. 1994 "Preparation of monolayer particle coated powder by the dry impact blending process utilizing mechanochemical treatment" Colloids Surf 82(2):117-128.
Nakagawa et al. "Encapsulation of Granules by Dry Blending Method and Drug Release" 1984 J. Pharm Dyn. s-31.
Yoshizawa and Koishi 1990 "The Coating and the Encapsulation of an Interactive Powder Mixture and its Application to Sustained Release Preparations" J Pharm Pharmacol 42:673-678.
Fairfax et al. 1984 "Comparison between the effects of inhaled isoprenaline and fenoterol on plasma cyclic AMP and heart rate in normal subjects" Br J Clin Pharmac 17:165-170.
List and Müller 1972 "Investigations about the FST complex" Pharmazeutische Industrie 34:963-971 (German / English translation).
Bolhuis et al. 1975 "Film formation by magnesium stearate during mixing and its effect on tabletting" Pharmaceutisch Weekblad 110:317-325.
Kikuta and Kitamori 1994 "Effect of mixing Time on the Lubricating Properties of Magnesium Stearate and the Final Characteristics of the compressed Tablets" Drug Development and Industrial Pharmacy 20(3):343-355.
Meakin et al. 1998 "The Effect of Flow Rate on Drug Delivery from the Pulvinal, a High-Resistance Dry Powder Inhaler" Journal of Aerosol Medicine 11(3):143-152.
Tanno, "Current Status of Mechanofusion Process for Producing Composite Particles" KONA Powder and Particle Journal, No. 8 (Jun. 1990).
Repertorio (Clenil Compositum Polvere), A-303-305.
Lewis and Train 1965 "The compaction of some solid lubricant materials" J Pharm Pharmacol 17:577-583.
Staniforth 1990 "Particle interactions in dry powder formulation of aerocolloidal suspensions" Respiratory Drug Delivery II Keystone, Colorado Mar. 26-30, 1990.
Staniforth et al. 1982 "Interparticle forces in binary and ternary ordered powder mixtures" J Pharm Pharmacol 34 (3):141-145.
Ganderton 1992 "The generation of respirable clouds from coarse powder aggregates" Journal of Biopharmaceutical Sciences 3(1/2):101-105.
Staniforth 1987 "Order out of chaos" J Pharm Pharmacol 39:329-334.
Colombo et al. 2000 "Surface smoothing of lactose particles for dry powder inhalers" Respiratory Drug Delivery VII, 629-631.
Raviraj Sukumar Pillai Dissertation 1993.
Hickey et al., 1988 "Preparation and Characterization of Disodium Fluorescein Powders in Association with Lauric and Capric Acids" Journal of Pharmaceutical Sciences 77:804-809 ("Hickey 1988").
Hickey 1990 "The Effect of Hydrophobic Coatings Upon the Behavior of Pharmaceutical Aerosol Powders" Aerosols: Science, Industry, Health and Environment. Pergamon Press, Oxford 1990; 1315-1318 ("Hickey 1990(b)").
Fults et al. 1997 "Effect of Particle Morphology on Emitted Dose of Fatty Acid-Treated Disodium Cromoglylate Powder Aerosols" Pharmaceutical Development and Technology, 2(1):67-79.
Hickey and Martonen 1993 "Behavior of hygroscopic Pharmaceutical Aerosols and the Influence of Hydrophobic Additives" Pharmaceutical Research 10:1-7.
Chow et al. 1985 "Modification of Acetaminophen Crystals: Influence of Growth in Aqueous Solutions Containing p-Acetoxyacetanilide on Crystal Properties" International Journal of Pharmaceutics, 24:239-258.
Chow et al. 1985 "Modification of Adipic Acid Crystals. II. Influence of Growth in the Presence of Oleic Acid on Crystal Properties" International Journal of Pharmaceutics, 25, 41-55.
Paramasivam and Vedaraman 1993 "Effect of Fatty Acid Additives on the Material Flow Properties of Dry Grinding" Powder Technology, 77:69-78.
"Final Report of the Safety Assessment of lithium Stearate, Aluminum Distearate, Aluminum Stearate, Aluminum Tristearate, Ammonium Stearate, Calcium Stearate, Magnesium Stearate, Potassium Stearate, Sodium Stearate, and Zinc Stearate" International Journal of Toxicology, 1:143-177.
Fueg et al. 1998 "Relationship Between Fine Particle Fraction and Percentage of Drug Retained After Air Jet Sieving of Model Carrier-Based Salbutamol Dry Powders for Inhalation" Abstracts of papers, Drug Delivery to the Lungs IX, The Aerosol Society, London, 64-67.
Keller et al. 1999 "Effect of Storage on the In-Vitro Performance of Formoterol-Fumarate Powder Blends in the SkyePharma mDPI" The Aerosol Society/Drug Delivery to the Lungs X: 41-44 ("Keller 1999").
Keller et al. 2000 "Effect of Storage on the In-Vitro Performance of Formoterol-Fumarate Powder Blends in the SkyePharma MDPI" Respiratory Drug Delivery VII, 511-514 ("Keller 2000").
Mueller-Walz et al. 2000 "Skye Protect—A Novel Approach to Improved Stability of Dry Powders for Inhalation" Proceedings, Drug Delivery to the Lungs XI Conference, 26-29.

* cited by examiner

METHOD OF MAKING PARTICLES FOR USE IN A PHARMACEUTICAL COMPOSITION

RELATED APPLICATIONS

This application is a continuation of U.S. application Ser. No. 13/623,326 filed Sep. 20, 2012, which is a continuation of U.S. application Ser. No. 12/767,530 filed Apr. 26, 2010, now U.S. Pat. No. 8,303,991 which is a continuation of U.S. application Ser. No. 10/433,072 filed Sep. 12, 2003, now U.S. Pat. No. 7,736,670 which is the United States national stage of International Application No. PCT/GB01/05315, filed Nov. 30, 2001, which was published under PCT Article 21 in English as International Publication No. WO 02/43701, and which claims benefit of British Application No. 0029261.5 filed, Nov. 30, 2000, British Application No. 0030946.8 filed Dec. 19, 2000, PCT Application No. PCT/GB01/01606 filed Apr. 9, 2001 and British Application No. 0124010.0 filed Oct. 5, 2001, the entire contents of which are hereby expressly incorporated herein by reference thereto.

The present invention relates to particles and to methods of making particles. In particular, the invention relates to methods of making composite active particles comprising a pharmaceutically active material for inhalation.

It is known to administer to patients drugs in the form of fine particles (active particles). For example, in pulmonary administration a particulate medicament composition is inhaled by the patient. Pulmonary administration is particularly suitable for medicaments which are intended to cure or alleviate respiratory conditions such as asthma and for medicaments which are not suitable for oral ingestion such as certain biological macromolecules. Known devices for the administration of drugs to the respiratory system include pressurised metered dose inhalers (pMDI's) and dry powder inhalers (DPI's).

The size of the active particles is of great importance in determining the site of the absorption. In order that the particles be carried deep into the lungs, the particles must be very fine, for example having a mass median aerodynamic diameter of less than 10 μm. Particles having aerodynamic diameters greater than 10 μare likely to impact the walls of the throat and generally do not reach the lung. Particles having aerodynamic diameters in the range of 5 μm to 0.5 μm will generally be deposited in the respiratory bronchioles whereas smaller particles having aerodynamic diameters in the range of 2 to 0.05 μm are likely to be deposited in the alveoli.

Such, small particles are, however, thermodynamically unstable due to their high surface area to volume ratio, which provides significant excess surface free energy and encourages particles to agglomerate. In the inhaler, agglomeration of small particles and adherence of particles to the walls of the inhaler are problems that result in the active particles leaving the inhaler as large agglomerates or being unable to leave the inhaler and remaining adhered to the interior of the inhaler.

In an attempt to improve that situation, dry powders for use in dry powder inhalers often include particles of an excipient material mixed with the fine particles of active material. Such particles of excipient material may be coarse, for example, having mass median aerodynamic diameters greater than 90μ, (such coarse particles are referred to as carrier particles) or they may be fine.

The step of dispersing the active particles from other active particles and from particles of excipient material, if present, to form an aerosol of fine active particles for inhalation is significant in determining the proportion of the dose of active material which reaches the desired site of absorption in the lungs. In order to improve the efficiency of that dispersal it is known to include in the composition additive materials. Such additive materials are thought to reduce the attractive forces between the particles thereby promoting their dispersal. Compositions comprising fine active particles and additive materials are disclosed in WO 97/03649.

Fine particles of active material suitable for pulmonary administration have often been prepared by milling, for example, jet milling. However, once the particles reach a minimum size referred to as the critical size, they re-combine at the same rate as being fractured, or do not fracture effectively and therefore do not reduce further in size. Thus, manufacture of fine particles by billing can require much effort and there are factors which consequently place limits on the minimum size of particles of active material which can be achieved, in practice, by such milling processes.

The present invention provides in a first aspect a method for making composite active particles for use in a pharmaceutical composition for pulmonary administration, the method comprising a milling step in which particles of active material are milled in the presence of particles of an additive material which is suitable for the promotion of the dispersal of the composite active particles upon actuation of an inhaler.

The method of the invention will, in general, produce composite active particles. The composite active particles are very fine particles of active material which have, upon their surfaces, an amount of the additive material. The additive material is preferably in the form of a coating on the surfaces of the particles of active material. The coating may be a discontinuous coating. The additive material may be in the form of particles adhering to the surfaces of the particles of active material. As explained below, at least some of the composite active particles may be in the form of agglomerates.

When the composite active particles are included in a pharmaceutical composition the additive material promotes the dispersal of the composite active particles on administration of that composition to a patient, via actuation of an inhaler. ("Actuation of an inhaler" refers to the process during which a dose of the powder is removed from its rest position in the inhaler. That step takes place after the powder has been loaded into the inhaler ready for use.) The effectiveness of that promotion of dispersal has been found to be enhanced in comparison to a composition, made by simple blending of similarly sized particles of active material with additive material.

The presence of the additive material on the surfaces of the particles of active material may confer controlled or delayed release properties and may provide a barrier to moisture.

It has also been found, that the milling of the particles of active material in the presence of an additive material produces significantly smaller particles and/or requires less time and less energy than the equivalent process carried out in the absence of the additive material. Using the method, of the invention, it has been possible to produce composite active particles which have a mass median aerodynamic diameter (MMAD) or a volume median diameter (VMD) of less than 1 μm. It is often not possible to make such small particles by other milling methods.

It is known that a milling process will tend to generate and increase the level of amorphous material on the surfaces of the millied particles thereby making them more cohesive. In contrast, the composite active particles of the invention will often be found to be less cohesive after the milling treatment.

The word "milling" as used herein refers to any mechanical process which applies sufficient force to the particles of active material that it is capable of breaking coarse particles (for example, particles of mass medium aerodynamic diameter greater than 100 μm) down to fine particles of mass median aerodynamic diameter not more than 50 μm or which applies a relatively controlled compressive force as described below in relation to the Mechano-Fusion and Cyclomix methods. It has been found that processes such as blending which do not apply a high degree of force are not effective in the method of the invention. It is believed that is because a high degree of force is required to separate the individual particles of active material and to break up tightly bound agglomerates of the active particles such that effective mixing and effective application of the additive material to the surfaces of those particles is achieved. It is believed that an especially desirable aspect of the milling process is that the additive material may become deformed in the milling and may be smeared over or fused to the surfaces of the active particles. It should be understood, however, that in the case where the particles of active material are already fine, for example, having a mass median aerodynamic diameter below 20μ prior to the milling step, the size of those particles may not be significantly reduced. The important thing is that the milling process applies a sufficiently high degree of force or energy to the particles.

The method of the invention generally involves bringing the additive particles into close contact with the surfaces of the active particles. In order to achieve coated particles, a degree of intensive mixing is required to ensure a sufficient break-up of agglomerates of both constituents, dispersal and even distribution of additive over the host active particles.

Where the additive particles are very small (typically <1 micron), generally less work is required, firstly as it is not required to break or deform but only to deagglomerate, distribute and embed the additive particles onto the active particle and secondly because of the naturally high surface energies of such small additive particles. It is known that where two powder components are mixed and the two components differ in size, there is a tendency for the small particles to adhere to the large particles (to form so called 'ordered mixes'). The short range Van der Waals interactions for such very fine components may be sufficient to ensure adhesion. However, where both, additive and active particles are very fine (for example less than 5 microns) a substantial degree of mixing will be required to ensure a sufficient break-up of agglomerates of both constituents, dispersal and even distribution of additive particles over the active particles as noted above. In some cases a simple contact adhesion may be insufficient and a stronger embedding or fusion of additive particles onto active particles is required to prevent segregation, or to enhance the structure and functionality of the coating.

Where the additive particles are not so small as to be sufficiently adhered by Van der Waals forces alone, or where there are advantages to distorting and/or embedding the additive particles substantially onto the host active particle, a greater degree of energy is required from the milling. In this case, the additive particles should experience sufficient force to soften and/or break, to distort and to flatten them. These processes are enhanced by the presence of the relatively harder active particles which act as a milling media as well as a de-agglomerating media for such processes. As a consequence of this process the additive particles may become wrapped around the core active particle to form a coating. These processes are also enhanced by the application of a compressive force as mentioned above.

As a consequence of the milling step, complete or partial, continuous or discontinuous, porous or non-porous coatings may be formed. The coatings originate from a combination of active and additive particles. They are not coatings such as those formed by wet processes that require dissolution of one or both components. In general, such wet coating processes are likely to be more costly and more time consuming than the milling process of the invention and also suffer from the disadvantage that it is less easy to control the location and structure of the coating.

A wide range of milling devices and conditions are suitable for use in the method of the invention. The milling conditions, for example, intensity of milling and duration, should be selected to provide the required degree of force. Ball milling is a preferred method. Centrifugal and planetary ball milling are especially preferred methods. Alternatively, a high pressure homogeniser may be used in which a fluid containing the particles is forced through a valve at high pressure producing conditions of high shear and turbulence. Shear forces on the particles, impacts between the particles and machine surfaces or other particles and cavitation due to acceleration of the fluid may all contribute to the fracture of the particles and may also provide a compressive force. Such homogenisers may be more suitable than ball mills for use in large scale preparations of the composite active particles. Suitable homogensiers include EmulsiFlex high pressure homogenisers which are capable of pressures up to 4000 Bar, Niro Soavi high pressure homogenisers (capable of pressures up to 2000 Bar), and Microfluidics Microfluidisers (maximum pressure 2750 Bar). The milling step may, alternatively, involve a high energy media mill or an agitator head mill, for example, the Netzch high energy media mill, or the DYNO-mill (Willy A. Bachofen AG, Switzerland). Alternatively the milling may be a dry coating high energy process such as a Mechano-Fusion system (Hosokawa Micron Ltd) or a Hybridizer (Nara). Other possible milling devices include air jet mills, pin mills, hammer mills, knife mills, ultracentrifugal mills and pestle and mortar mills.

Especially preferred methods are those involving the Mechano-Fusion, Hybridiser and Cyclomix instruments.

Preferably, the milling step involves the compression of the mixture of active and additive particles in a gap (or nip) of fixed, predetermined width (for example, as in the Mechano-Fusion and Cyclomix methods described below).

Some preferred milling methods will now be described in greater detail.

Mechano-Fusion:

As the name suggests, this dry coating process is designed to mechanically fuse a first material onto a second material. The first material is generally smaller and/or softer than the second. The Mechano-Fusion and Cyclomix working principles are distinct from alternative milling techniques in having a particular interaction between inner element and vessel wall, and are based on providing energy by a controlled and substantial compressive force.

The fine active particles and the additive particles are fed into the Mechano-Fusion driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall). The particles violently collide against each other with enough energy to locally heat and soften, break, distort, flatten and wrap the additive particles around the core particle to form a coating. The energy is generally sufficient to break up agglomerates and some degree of size reduction of both components may occur. Embedding and fusion of additive particles onto the active particles may occur, and may be facilitated by the relative differences in hardness (and optionally size) of the two components. Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball and media mills. Also, in general, no impaction of milling media surfaces is present so that wear and consequently contamination are minimised. The speed of rotation may be in the range of 200 to 10,000 rpm. A scraper may also be present to break up any caked material building up on the vessel surface. This is particularly advantageous when using fine cohesive starting materials. The local temperature may be controlled by use of a heating/cooling jacked built into the drum vessel walls. The powder may be recirculated through the vessel.

Cyclomix Method (Hosokawa Micron):

The Cyclomix comprises a stationary conical vessel with a fast rotating shaft with paddles which move close to the wall. Due to the high rotational speed of the paddles, the powder is propelled towards the wall, and as a result, the fixture experiences very high shear forces and compressive stresses between wall and paddle. Such effects are similar to the Mechano-Fusion as described above and may be sufficient to locally heat and soften, to break, distort, flatten and wrap the additive particles around the active particles to form a coating. The energy is sufficient to break up agglomerates and some degree of size reduction of both components may also occur depending on the conditions and upon the size and nature of the particles.

Hybridiser Method:

This is a dry process which can be described as a product, embedding or filming of one powder onto another. The fine active particles and fine or ultra fine additive particles are fed info a conventional high shear mixer pre-mix system to form an ordered mixture. This powder is then fed into the Hybridiser. The powder is subjected to ultra-high speed impact, compression and shear as it is impacted by blades on a high speed rotor inside a stator vessel, and is re-circulated within the vessel. The active and additive particles collide with each other. Typical speeds of rotation are in the range of 5,000 to 20,000 rpm. The relatively soft fine additive particles experience sufficient impact force to soften, break, distort, flatten and wrap around the active particle to form a coating. There may also be some degree of embedding into the surface of the active particles.

Other preferred methods include ball and high energy media mills which are also capable of providing the desired high shear force and compressive stresses between surfaces, although as the clearance gap is not controlled, the coating process may be less well controlled than for Mechano-Fusion milling and some problems such as a degree of undesired re-agglomeration may occur. These media mills may be rotational, vibrational, agitational, centrifugal or planetary in nature.

It has been observed in some cases that when ball milling active particles with additive material, a fine powder is not produced. Instead the powder was compacted on the walls of the mill by the action of the mill. That has inhibited the milling action and prevented the preparation of the composite active particles. That problem, occurred particularly when certain additive materials were used, in cases where the additive material was present in small proportions (typically <2%), in cases where the milling balls were relatively small (typically <3 mm), in cases where the milling speed was too slow and where the starting particles were too fine. To prevent this occurring it is advantageous to ball mill in a liquid medium. The liquid medium reduces the tendency to compaction, assists the dispersal of additive material and improves any milling action.

It has been found to be preferable to use a large number of fine milling balls, rather than fewer heavy balls. The finer balls perform a more efficient co-milling action. Preferably the balls have a diameter of less than 5 mm, advantageously less than 2 mm. Liquid media are preferred which do not dissolve the active material and which evaporate rapidly and fully, for example non-aqueous liquids such as diethylether, acetone, cyclohexane, ethanol, isopropanol or dichloromethane. Liquid media are preferred which are non flammable, for example dichloromethane and fluorinated hydrocarbons, especially fluorinated hydrocarbons which are suitable for use as propellants in inhalers.

Pestle and mortar mills are other mills which also provide a very high shear force and compressive stresses between surfaces.

Mechano-Micros and Micros mills made by Nara (where particles are compressed by rotating grinding rings) may also be used. Mills referred to impact mixers, attrition mills, pin mills and disc mills may also be used.

The mass median aerodynamic diameter of the particles of active material may be substantially reduced during the milling step especially when the active material is in the form of coarse particles prior to the milling step. The mass median aerodynamic diameter (MMAD) of the particles of active material may be reduced by at least 10%, by at least 50%, or by at least 70% during the milling step depending on the milling conditions and the MMAD of the active particles prior to the milling step.

Advantageously, after the milling step, the MMAD of the active particles is less than 9 μm, preferably less then 4 μm and more preferably less then 2 μm.

In a similar way, where the additive material is in the form of coarse particles prior to the milling step, their MMAD will be substantially reduced during the milling step. The MMAD of the particles of additive material may be reduced by at least 10%, at least 50% or at least 70% during the milling step, depending on the milling conditions and on the MMAD of the particles of additive material before the milling step. The size of the additive particles after the milling step is preferably significantly less than the size of the active particles, to enable the additive materials to more effectively coat the surfaces of the active particles. In practice, that difference in size between the active particles and additive particles is likely to be achieved as a consequence of the milling because the additive material will usually be more easily fractured or deformed than the active material and so will be broken into smaller particles than the active material. As noted above, the particles of additive material preferably become smeared over or fused to the surfaces of the particles of active material, thereby forming a coating which may be substantially continuous or discontinuous. Where the coating is discontinuous, it preferably covers, on average, at least 50% (that is, at least 50% of the total surface area of the active particles will be covered by additive material), more advantageously at least 70% and most preferably at least 90% of the surfaces of the active particles. The coating is preferably on average less than 1 μm, more preferably less than 0.5 μm and most preferably less than 200 nm thick.

The milling step may be carried out in a closed vessel, for example in a ball mill or a Mechano-Fusion device. The use of a closed vessel prevents loss of ultrafine particles or vapour of the additive material which has been found to occur in jet milling or other open processes. Preferably, the milling is not jet milling (micronisation).

The milling may be wet milling, that is, the milling step may be carried out in the presence of a liquid. That liquid medium, may be high or low volatility and of any solid content as long as it does not dissolve the active particles to any significant degree and its viscosity is not so high that it prevents effective milling. The liquid medium preferably is not aqueous. The liquid is preferably one in which the additive material is substantially insoluble but some degree of solubility may be acceptable as long as there is sufficient additive material present that undissolved particles of additive material remain. The presence of a liquid medium helps to prevent compacting of the particles of active material on the walls of the vessel and may also allow the more even spreading of the additive material on the surface of the particles of active material as compared to dry milling.

It has been found that the Mechano-Fusion and Cyclomix techniques referred to above often provide the composite active particles as individual, that is, unagglomerated composite active particles. That is in contrast to less controlled methods such as ball milling, which have been found to often produce the composite active particles in the form of agglomerated composite active particles.

The mass median aerodynamic diameter of the composite active particles is preferably not more than 10 μm, and advantageously it is not more than 5 μm, more preferably not more than 3 μm and most preferably not more than 1 μm. Accordingly, advantageously at least 90% by weight of the composite active particles have a diameter of not more than 10 μm, advantageously not more than 5 μm, preferably not more than 3 μm and more preferably not more than 1 μm. Advantageously, after the milling step, the active particles will be of a suitable size for inhalation to the desired part of the lung, for example, having an MMAD in the range of 3 to 0.1 μm for absorption in the deep lung, 5 to 0.5 μm for absorption in the respiratory bronchioles, 10 to 2 μm for delivery to the higher respirator system and 2 to 0.05 μm for delivery to the alveoli. Accordingly, advantageously the diameter of at least 90% by weight of the composite active particles have an aerodynamic diameter in the range of 3 to 0.1 μm, preferably 5 to 0.5 μm, advantageously 10 to 2 μm, and especially advantageously 2 to 0.05 μm. The MMAD of the active particles will not normally be lower than 0.01 μm.

As mentioned above, the composite active particles produced after the milling step may be of a suitable size for delivery to the desired part of the respiratory system.

However, the composite active particles may be smaller than that suitable size or at least some of the composite active particles may, after the milling step, be in the form of agglomerates which are larger than the suitable size. The method therefore preferably also comprises, after the milling step, a processing step in which the degree of agglomeration of the composite active particles is changed. The processing step may be an agglomeration step in which the particles of active material agglomerate to form agglomerated composite active particles. In that way agglomerates of a size tailored to the requirement may be produced. Whilst any method of agglomeration can be used, for example, granulation, preferably, the composite active particles are agglomerated in a drying step (as described below) to form agglomerated composite active particles. Preferably, the agglomeration step is a spray drying step. The spray drying conditions may be selected to produce droplets having a desired size in the range of 1000 μm to 0.5 μm. The size of the agglomerates produced will depend largely on the concentration of the composite active particles in the spray feed and the droplet size. Other materials, for example, binders may be included in the spray feed. Where the milling step involves wet milling, the suspension or slurry may be spray dried directly after the milling step. Agglomeration may also be conducted in a fluid bed dryer or granulator.

Where, after the milling step, at least some of the composite active particles are in the form of agglomerates and it is desired to break those agglomerates down or to reduce their size, the processing step may be a deagglomeration step. The deagglomeration step may involve mechanical breaking up of the unwanted agglomerates, for example, by forcing them through a sieve or by subjecting them to a treatment in a dry fluidised bed, a jet mill, a ball mill or other form of milling device. The intensity and/or duration of that treatment step will, in general, be less that, of the milling step. The deagglomeration step may also be a spray drying step because, whilst spray drying as a drying step is particularly useful in preparing agglomerated composite active particles, by appropriate control of the conditions it is possible to produce the composite active particles largely as single particles rather than as agglomerates.

The term "agglomerated composite active particles" refers to particles which consist of more than one composite active particle, those composite active particles being adhered to each other. Where the agglomerated particles are for inhalation they will preferably have a MMAD which renders them suitable for deposition in the desired part of the lung.

Preferably, the method comprises, after the milling step, a drying step in which a mixture of the composite active particles and a liquid is dried to remove the liquid. The mixture may be in the form of a slurry or suspension. During the drying step, especially when spray drying is used, the degree of agglomeration of the composite active particles may change, in which case the drying step is the same step as the processing step mentioned above. However, the drying step may be included for other reasons, for example, when the milling is wet milling, and it is desired to produce the composite active particles as a dry powder.

The drying step may involve filtration followed by drying, or evaporation of the liquid. Preferably, the drying step is a spray drying step. Alternatively, the liquid may be evaporated slowly or the drying step may be a freeze drying step.

The milling is preferably dry, that is to say, there is no liquid present during the milling and the mixture to be milled is in the form of a dry particulate. In that case, liquid may be added after the milling step, usually in order that a drying step be used to form agglomerated composite active particles, as described above.

Advantageously, the milling step is carried out at a reduced temperature, for example, below 10° C. and preferably below 0° C. Such low temperature conditions may increase the efficiency of the milling step and/or reduce decomposition of the active material.

The optimum amount of additive material will depend on the chemical composition and other properties of the additive material and upon the nature of the active material and/or excipient material. In general, the amount of additive material in the composite particles will be not more than 60% by weight, based on the weight of the active material and/or excipient material. However, it is thought that for most additive materials the amount of additive material should be in the range of 40% to 0.25%, preferably 30% to 0.5%, more preferably 20% to 2%, based on the total weight of the additive material and the active material being milled. In general, the amount of additive material is at least 0.01% by weight based on the weight of the active material.

The terms "additive particles" and "particles of additive material" are used interchangeably herein. The additive particles comprise one or more additive materials. Preferably, the additive particles consist essentially of the additive material.

Advantageously the additive material is an anti-adherent material and will tend to decrease the cohesion between the composite active particles and between the composite active particles and any other particles present in the pharmaceutical composition.

Advantageously the additive material is an anti-friction agent (glidant) and will give better flow of the pharmaceutical composition in, for example, a dry powder inhaler which will lead to a better dose reproducibility.

Where reference is made to an anti-adherent material, or to an anti-friction agent, the reference is to include those materials which are able to decrease the cohesion between the particles, or which will tend to improve the flow of powder in an inhaler, even though they may not usually be referred to as anti-adherent material or an anti-friction agent. For example, leucine is an anti-adherent material as herein defined and is generally thought of as an anti-adherent material but lecithin is also an anti-adherent material as herein defined, even though it is not generally thought of as being anti-adherent, because it will tend to decrease the cohesion between the composite active particles and between the composite active particles and any other particles present in the pharmaceutical composition.

The additive material may include a combination of one or more materials.

It will be appreciated that the chemical composition of the additive material is of particular importance. Preferably, the additive material is a naturally occurring animal or plant substance.

Advantageously, the additive material includes one or more compounds selected from amino acids and derivatives thereof, and peptides and derivatives thereof. Amino acids, peptides and derivatives of peptides are physiologically acceptable and give acceptable release of the active particles on inhalation.

It is particularly advantageous for the additive material to comprise an amino acid. The additive material may comprise one or more of any of the following amino acids: leucine, isoleucine, lysine, valine, methionine, phenylalanine. The additive may be a salt or a derivative of an amino acid, for example aspartame or acesulfame K. Preferably, the additive particles consist substantially of an amino acid, more preferably of leucine, advantageously L-leucine. The D- and DL-forms may also be used. As indicated above, leucine has been found to give particularly efficient dispersal of the active particles on inhalation.

The additive material may include one or more water soluble substances. This helps absorption of the substance by the body if the additive reaches the lower lung. The additive material may include dipolar ions, which may be zwitterions.

Alternatively, the additive material may comprise a phospholipid or a derivative thereof. Lecithin has been found to be a good material for the additive material.

Preferably, the additive material comprises a metal stearate, or a derivative thereof, for example, sodium stearyl fumarate or sodium stearyl lactylate. Advantageously, the additive material comprises a metal stearate. For example, zinc stearate, magnesium stearate, calcium stearate, sodium stearate or lithium stearate. Preferably, the additive material comprises magnesium stearate.

The additive material may include or consist of one or more surface active materials, in particular materials that are surface active in the solid state, which may be water soluble, for example lecithin, in particular soya lecithin, or substantially water insoluble, for example solid state fatty acids such as oleic acid, lauric acid, palmitic acid, stearic acid, erucic acid, behenic acid, or derivatives (such as esters, and salts) thereof such as glyceryl behenate. Specific examples of such materials are: phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general.

Other possible additive materials include sodium benzoate, hydrogenated oils which are solid at room temperature, talc, titanium dioxide, aluminium dioxide, silicon dioxide and starch.

The additive material preferably comprises one or more materials selected from the group consisting of amino acids, lecithins, phospholipids, sodium stearyl fumarate, glyceryl behenate and metal stearates (especially magnesium stearate).

The terms “active particles” and “particles of active material” are used interchangeably herein. The active particles referred to throughout the specification will comprise one or more pharmacologically active agents. The active particles advantageously consist essentially of one or more pharmacologically active agents. Suitable pharmacologically active agents may be materials for therapeutic and/or prophylactic use. Active agents which may be included in the formulation include those products which are usually administered orally by inhalation for the treatment of disease such as respiratory disease, for example, β-agonists.

The active particles may comprise at least one $\beta_2$-agonist, for example one or more compounds selected from terbutaline, salbutamol, salmeterol and formetorol. If desired, the active particles may comprise more than one of those active agents, provided that they are compatible with one another under conditions of storage and use. Preferably, the active particles are particles of salbutamol sulphate. References herein to any active agent is to be understood to include any physiologically acceptable derivative. In the case of the $\beta_2$-agonists mentioned above, physiologically acceptable derivatives include especially salts, including sulphates.

The active particles may be particles of ipatropium bromide.

The active particles may include a steroid, which may be beclomethasone dipropionate or may be Fluticasone. The active principle may include a cromone which may be sodium cromoglycate or nedocromil. The active principle may include a leukotriene receptor antagonist.

The active particles may include a carbohydrate, for example heparin.

The active particles may advantageously comprise a pharmacologically active agent for systemic use and advantageously they are capable of being absorbed into the circulatory system via the lungs. For example, the active particles may comprise peptides or polypeptides such as Dnase, leukotrienes or insulin. The pharmaceutical compositions of the invention may in particular have application in the administration of insulin to diabetic patients, preferably avoiding the normally invasive administration techniques used for that agent. The composite active particles could also be used for the local administration of other agents for example for pain relief (e.g. analgesics such as Fentanyl or dihydroergotamine which is used for the treatment of migraine), anti cancer activity, anti-virals, antibiotics or the local delivery of vaccines to the respiratory tract.

Whilst it will often be desired to obtain the composite active particles in dry form, as described above, where the pharmaceutical composition is one comprising a liquid, for example, as propellant, it may be preferable for the active particles to be milled in the presence of that liquid and to omit the drying step, simply using the slurry or suspension of the composite active particles in the liquid as an ingredient in the pharmaceutical composition. Thus for example, where the pharmaceutical composition is for use in a pMDI, the active particles and the additive material may be milled in the presence of liquid propellant (under pressure or at below room temperature if necessary). The resulting slurry may be used directly in a pMDI or further materials may be added, for example, more propellant, surfactants, or co-solvents.

Accordingly, the invention also provides, in one embodiment, a method of making composite active particles for use in a pharmaceutical composition, the method comprising a milling step in which particles of active material are milled in the presence of a liquid and an additive material which is suitable for the promotion of the dispersal of the composite active particles upon actuation of a delivery device.

Preferably, the liquid comprises a propellant suitable for use in a pMDI. Suitable propellants include CFC-12, HFA-134a, HFA-227, HCFC-22 (difluorochlormethane), HCFC-123 (dicholorotrifluorethane), HCFC-124 (chlorotetrafluoroethane), dimethyl ether, propane, n-butane, isobutane, HFA-125 (pentafluoroethane) and HFA-152 (difluoroethane). If however, it is desired to isolate the dry composite active particles (or agglomerates thereof) the method may also include a drying step, preferably a spray drying step. Accordingly, in a further embodiment, the invention provides a method of making composite active particles for use in a pharmaceutical composition, the method comprising a wet milling step in which the particles of active material are milled in the presence of a liquid and an additive material which is suitable for the promotion of the dispersal of the composite active particles upon actuation of a delivery device; and a drying step in which the liquid is removed.

As explained above, the conditions of the drying step, which is preferably a spray drying step, may be chosen either to provide agglomerated composite active particles of a desired size or to provide substantially unagglomerated particles, that is, individual composite active particles. In some cases it may be preferable to perform the milling step in the absence of liquid, (dry milling). The composite active particles may then be agglomerated by mixing with a liquid and drying to give agglomerated composite active particles. Accordingly, in a further embodiment, the invention provides a method of making agglomerated composite active particles for use in a pharmaceutical composition, the method comprising:

a dry milling step in which particles of active material are milled in the presence of an additive material which is suitable for the promotion of the dispersal of the composite active particles upon actuation of a delivery device; and an agglomeration step, in which the composite active particles are mixed with a liquid and the mixture is dried to remove the liquid.

The invention also provides composite active particles for use in a pharmaceutical composition, preferably a pharmaceutical composition for inhalation, more preferably a powder for a dry powder inhaler.

The invention also provides composite active particles for use in a pharmaceutical composition, each composite active particle comprising a particle of active material and additive material on the surface of that particle of active material, the composite active particles having a mass median aerodynamic diameter of not more than 2 μm, the additive material being suitable for the promotion of the dispersal of the composite active particles upon actuation of a delivery device. Preferably, the composite active particles have a MMAD of not more than 1 μm, especially advantageously not more than 0.5 μm. As noted above, the composite particles may be in the form of agglomerated composite particles.

MMAD may be determined using an impinger, for example, a multi-stage liquid impinger. Volume median diameters and measurements of the proportion of particles having a diameter less than a certain value may be determined by the Malvern laser light scattering method.

Advantageously, the composite active particles do not comprise significant amounts (more than 10% by weight) of a polymer of a type which would result in the particles becoming sticky. Such polymers include polymers of a alpha-hydroxycarboxylic acid, for example, polylactic acid, copolymers of lactic acid and block copolymers such as ethylene oxide/propylene oxide block copolymers or poloxamines.

The invention further provides a pharmaceutical composition comprising composite active particles. Preferably, the pharmaceutical composition is a dry powder and is suitable for use in a dry powder inhaler. Such pharmaceutical compositions may comprise essentially only the composite active particles or they may comprise additional ingredients such as carrier particles and flavouring agents. Carrier particles may be of any acceptable excipient material or combination of materials. For example, the carrier particles may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously the carrier particles are of a polyol. In particular the carrier particles may be particles of crystalline sugar, for example mannitol, dextrose or lactose. Preferably, the carrier particles are of lactose.

Advantageously, substantially all (by weight) of the carrier particles have a diameter which lies between 20 μm and 1000 μm, more preferably 50 μm and 1000 μm. Preferably, the diameter of substantially all (by weight) of the carrier particles is less than 355 μm and lies between 20 μm and 250 μm. Preferably at least 90% by weight of the carrier particles have a diameter between from 60 μm to 180 μm. The relatively large diameter of the carrier particles improves the opportunity for other, smaller particles to become attached to the surfaces of the carrier particles and to provide good flow and entrainment characteristics and improved release of the active particles in the airways to increase deposition of the active particles in the lower lung.

The ratio in which the carrier particles (if present) and composite active particles are mixed will, of course, depend on the type of inhaler device used, the type of active particles used and the required dose. The carrier particles may be present in an amount of at least 50%, more preferably 70%, advantageously 90% and most preferably 95% based on the combined weight of the composite active particles and the carrier particles.

Where carrier particles are included in the pharmaceutical composition, that composition preferably also includes small excipient particles having, for example, a particle size between 5 to 20 µm. Preferably the small excipient particles are present in an amount of from 1% to 40%, more preferably 5% to 20% based on the weight of the carrier particles.

Compositions for use in a dry powder inhaler which include carrier particles will preferably include at least 2%, more preferably at least 5% and most preferably at least 10% by weight of the composite active particles based on the total mass of the composition. The composite active particles are especially suitable for dry powder compositions which do not include significant amounts of carrier particles and in such compositions the composite active particles will preferably be present in a proportion of at least 60%, more preferably at least 80% by weight based on the total weight of the composition.

The pharmaceutical composition may comprise a propellant and be suitable for use in a pressurised metered dose inhaler.

The invention also provides the use of an additive material as a milling aid in the milling of particles of active material. The term milling aid should be understood to refer to a substance which reduces the amount of energy required to mill the particles of active material and/or excipient material.

Embodiments of the invention will now be described for the purposes of illustration only with reference to the Figures in which:

FIG. 3 is a scanning electron micrograph of the composite active particles of Example 1a;

All percentages are by weight unless indicated otherwise.

EXAMPLE 1

Figure 1:
FIGS. 1 and 2 are scanning electron micrographs of the composite active particles of Example 1.
Figure 2:
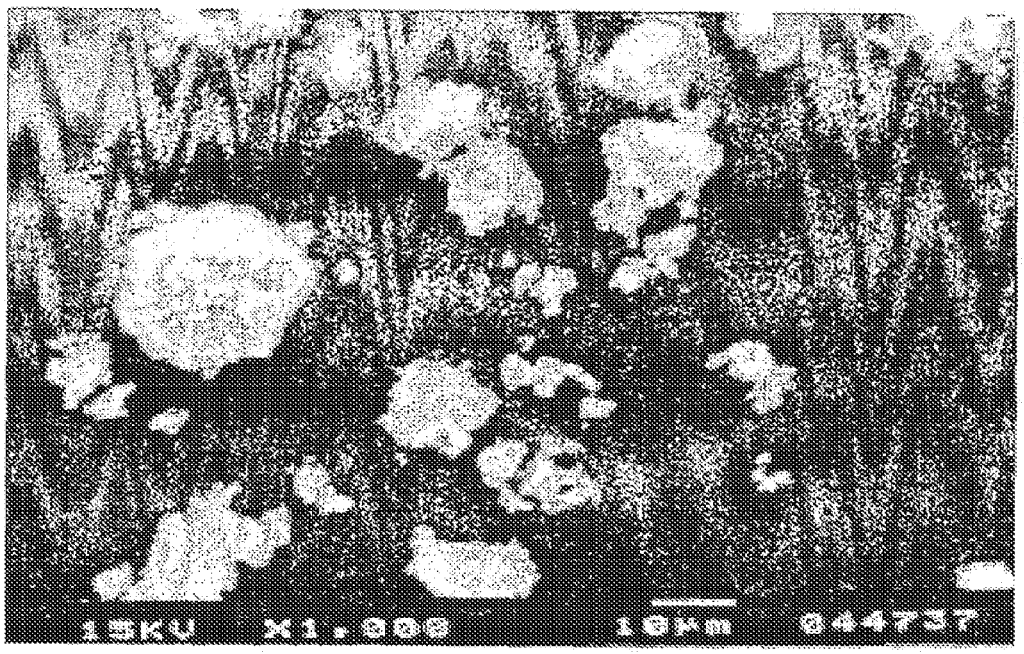

5 g of micronised salbutamol sulphate (particle size distribution: 1 to 5 µm) and 0.5 g of magnesium stearate were added to a 50 $cm^3$ stainless steel milling vessel together with 20 $cm^3$ dichloromethane and 124 g of 3 mm stainless steel balls. The mixture was milled at 550 rpm in a Retsch S100 Centrifugal Mill for 5 hours. The powder was recovered by drying and sieving to remove the mill balls. An electron micrograph of the powder is shown in FIG. 1. This was repeated 3 times using leucine in place of the magnesium stearate and an electron micrograph of the powder is shown in FIG. 2. The powders shown in FIGS. 1 and 2 appear to have particles in the size range 0.1 to 0.5 µm.

EXAMPLE 1a

Figure 3:
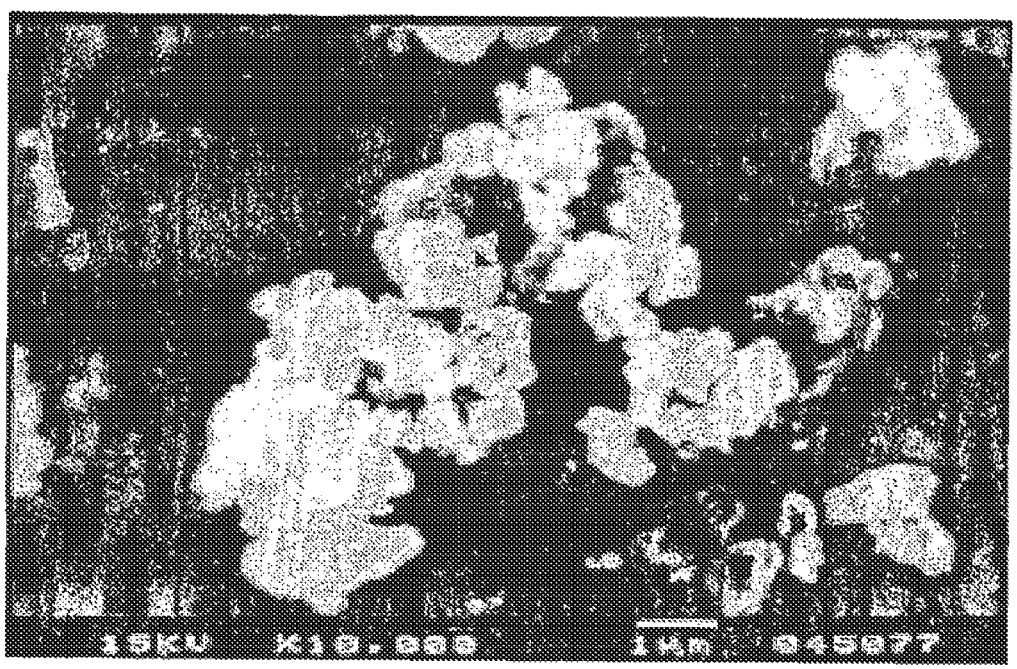

Micronised salbutamol sulphate and magnesium stearate were combined as particles in a suspension in the ratio 10:1 in propanol. This suspension was processed in an Emulsiflex C50 high pressure homogeniser by 5 sequential passes through the system at 25,000 psi. This dry material was then recovered by evaporating the propanol. The particles are shown in FIG. 3.

EXAMPLE 2

It was found that, on drying, the powder prepared in Example 1 including magnesium stearate as additive material formed assemblies of primary particles which were hard to deagglomerate. A sample of this powder was re-dispersed by ball milling for 90 minutes at 550 rpm in a mixture of ethanol, polyvinylpyrolidone (PVPK30) and HFA227 liquid propellant to give the following composition:

| | |
|---|---|
| 0.6% w/w | Salbutamol sulphate/magnesium stearate composite particles |
| 0.2% w/w | PVPK30 |
| 5.0% w/w | Ethanol |
| 94.2% w/w | HFA 227 |

(The PVP was included to stabilise the suspension of the composite particles in the ethanol/HFA227).

Figure 4:
FIG. 4 is a scanning electron micrograph of the composite particles of Example 2.
Figure 5:
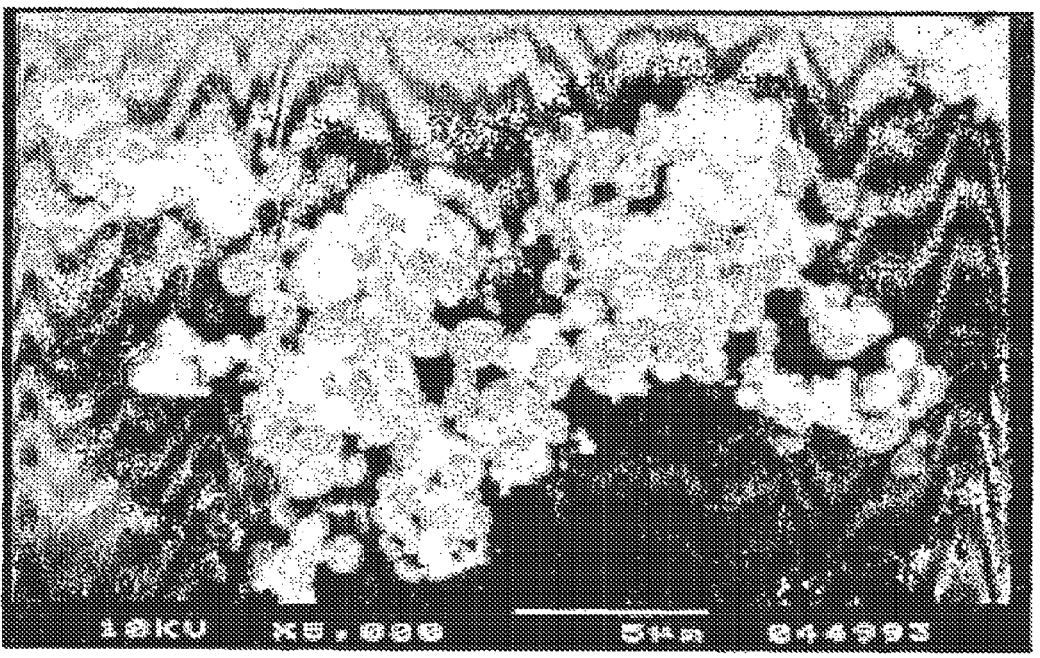
FIG. 5 is a scanning electron micrograph of the same sample of particles shown in FIG. 4 but at a higher magnification.

The suspension could be used directly as in a pMDI. In this example, however, the composition was sprayed from a pressurised can through an orifice −0.4 mm in diameter to produce dried composite active particles of salbutamol sulphate and magnesium stearate with PVP. Those particles (shown in FIGS. 4 and 5) were collected and examined and were found to be in the aerodynamic size range 0.1 to 4 µm.

EXAMPLE 3

The process of Example 2 was repeated except that the composition was as follows:

| | |
|---|---|
| 3% w/w | Salbutamol sulphate/magnesium stearate composite particles |
| 1% w/w | PVPK30 |
| 3% w/w | Ethanol |
| 93% w/w | HFA 227 |

Figure 6:
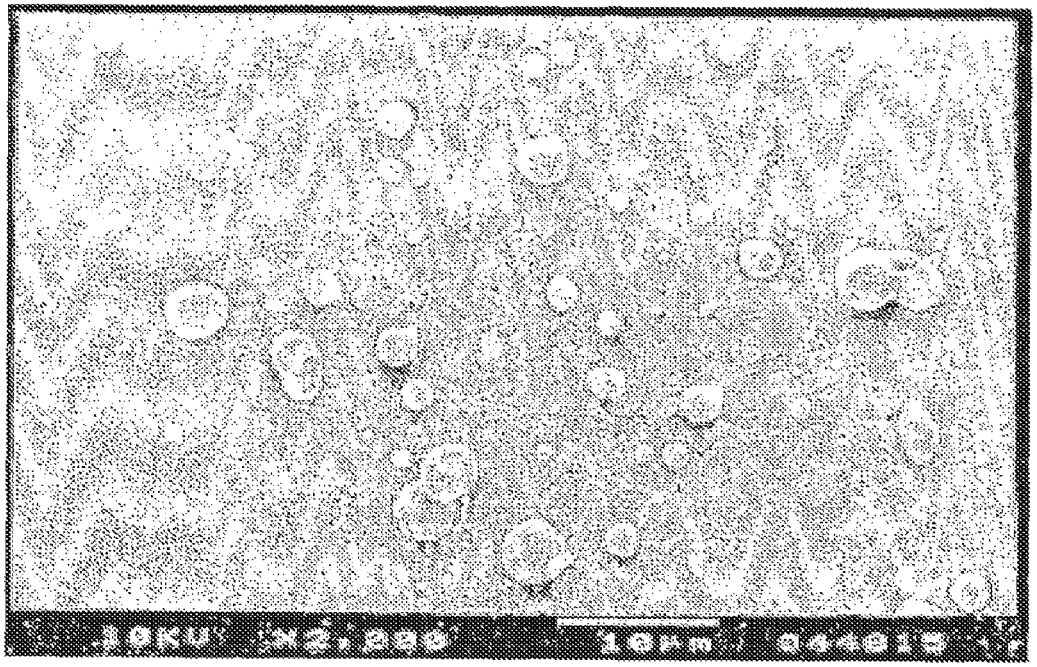
FIG. 6 is a scanning electron micrograph of the composite particles of Example 3.
Figure 7:
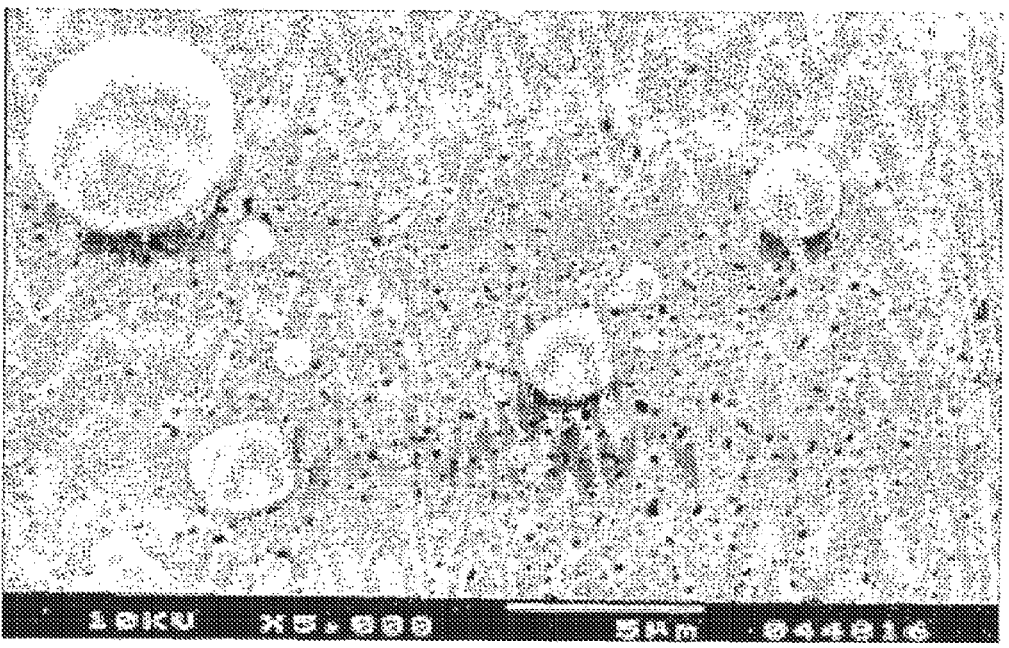
FIG. 7 is a scanning electron micrograph of the same sample of particles shown in FIG. 6 but at a higher magnification.

The particles produced are shown in FIGS. 6 and 7.

EXAMPLE 4

Salbutamol Sulphate/Magnesium Stearate Blends a) Homogenised Magnesium Stearate 240 g magnesium stearate (Riedel de Haen, particle size by Malvern laser diffraction:$d_{50}$=9.7 μm) was suspended in 2150 g dichloroethane. That suspension was then mixed for 5 minutes in a Silverson high shear mixer. The suspension was then processed in an Emulsiflex C50 high pressure homogeniser fitted with a heat exchanger at 10000 psi for 20 minutes in circulation mode (300 $cm^3$/min) for 20 minutes. The suspension was then circulated at atmospheric pressure for 20 minutes allow it to cool. The next day, the suspension was processed in circulation mode (260 $cm^3$/min) at 20000 psi for 30 minutes. The dichloroethane was removed by rotary evaporation followed by drying in a vacuum over at 37° C. overnight. The resulting cake of material was broken up by ball milling for 1 minute. The homogenised magnesium stearate had a particle size of less than 2 μm.

b) A 9:1 by weight blend of salfoutamol sulphate and homogenised magnesium stearate having a particle size of less than 2 μm was prepared by blending the two materials with a spatula. An electron micrograph of the blended material showed that the blend was mostly in the form of agglomerated particles, the agglomerates having diameters of 50 μm and above. The blend was then processed in a Mechano-Fusion mill (Hosokawa) as follows:

| Machine data: | Hosokawa Mechano-Fusion: | AMS-Mini |
|---|---|---|
| | Drive: | 2.2 kW |
| | Housing: | stainless steel |
| | Rotor: | stainless steel |
| | Scraper: | None |
| | Cooling: | Water |
| | Gas purge: | None |

Figure 8:
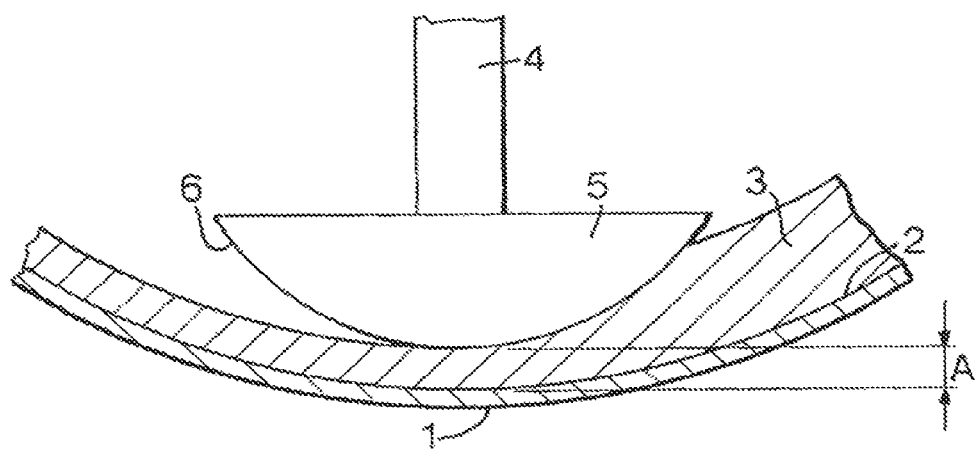
FIG. 8 is a schematic drawing of part of a Mechano-Fusion machine.

The Mechano-Fusion device (see FIG. 8) comprises a cylindrical drum 1 having an inner wall 2. In use, the drum rotates at high speed. The powder 3 of the active and additive particles is thrown by centrifugal force against the inner wall 2 of the drum 1. A fixed arm 4 projects from the interior of the drum in a radial direction. At the end of the arm closest to the wall 2, the arm is provided with a member 5 which presents an arcuate surface 6, of radius of curvature less than that of inner wall 2, toward that inner wall. As the drum 1 rotates, it carries powder 3 into the gap between arcuate surface 6 and inner wall 2 thereby compressing the powder. The gap is of a fixed, predetermined width A. A scraper (not shown in FIG. 8) may be provided to scrape the compressed powder from the wall of the drum.

All samples were premixed for 5 minutes by running the machine at 1000 rpm. The machine speed was then increased to 5050 rpm for 30 minutes. The procedure was repeated for salbutamol sulphate/magnesium stearate in the following weight ratios: 19:1, 3:1, 1:1.

Figure 9:
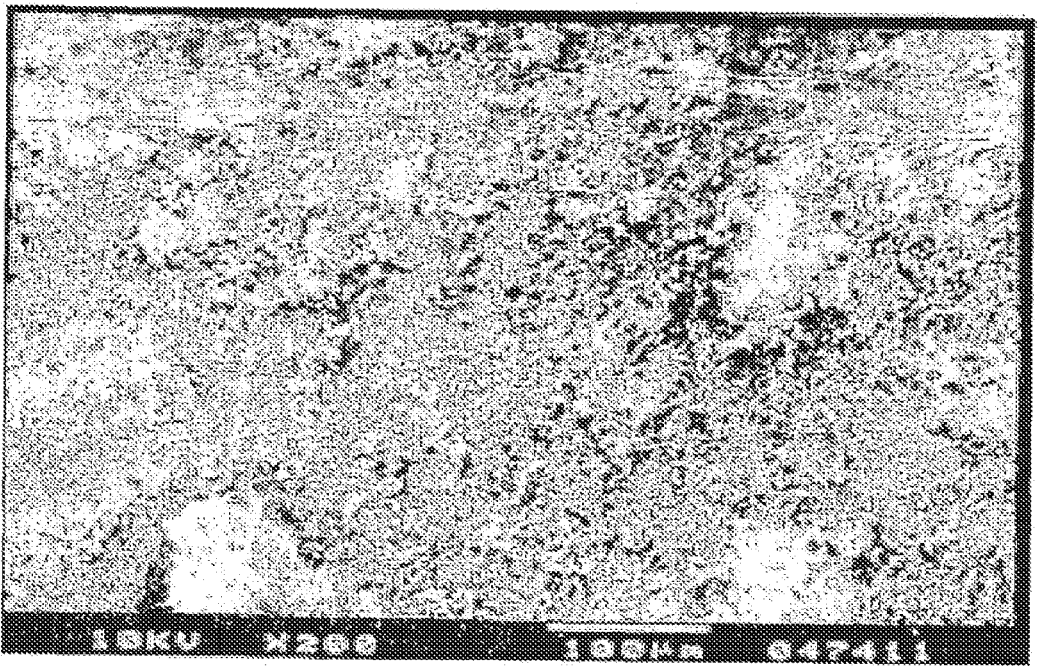
FIGS. 9 and 10 are electromicrographs of composite active particles according to the invention comprising salbutamol sulphate and magnesium stearate in a ratio of 19:1 (Example 4).
Figure 10:
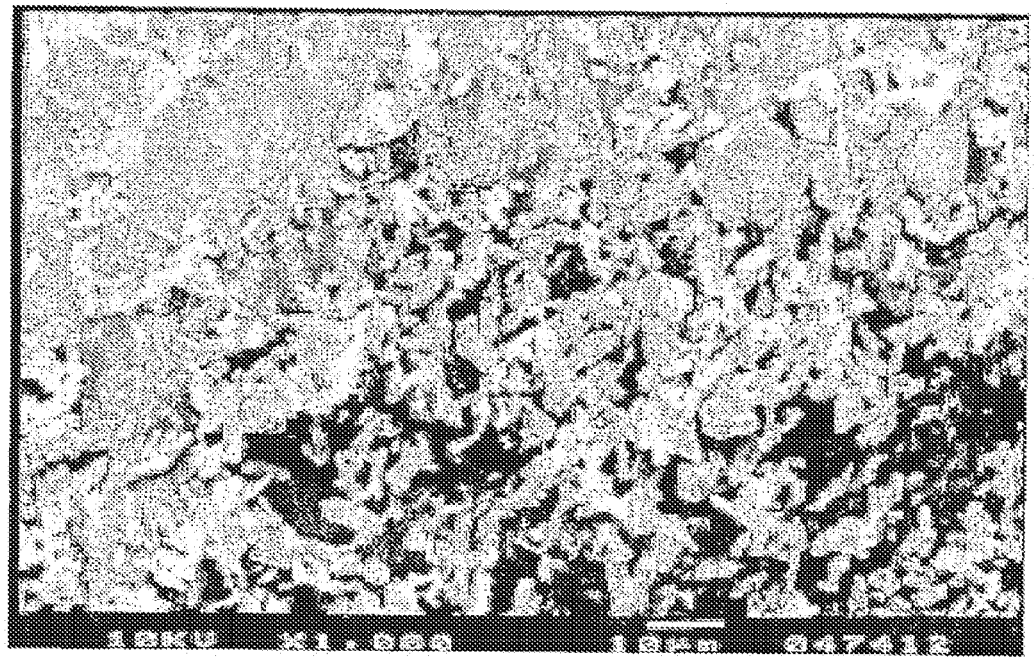

Electronmicrographs of the 19:1 processed material are shown in FIGS. 9 and 10 and indicate that the material was mostly in the form of simple small particles of diameter less than 5 μm or in very loose agglomerates of such particles with only one agglomerate of the original type being visible.

The 3:1 and the 19:1 blends were then each loaded into a 20 mg capsule and fired from a twin stage impinger. A sample of unprocessed salbutamol sulphate was also fired from the TSI to provide a comparison.

The fine particle fractions were then calculated and are given in table 1.

TABLE 1

Fine Particle Fraction results for salbutamol sulphate blends.

| Composition | Fine Particle Fraction % |
|---|---|
| salbutamol sulphate | 28 |
| salbutamol sulphate/ magnesium stearate 19:1 | 66 |
| salbutamol sulphate/ magnesium stearate 3:1 | 66 |

EXAMPLE 5

Micronised glycopyrrolate and homogenised magnesium stearate (as described in Example 4) were combined in a weight ratio of 75:25. This blend (~20 g) was then milled in the Mechano-Fusion AMS-Mini system as follows. The powder was pre-mixed for 5 minutes at ~900 rpm. The machine speed was then increased to ~4,800 rpm for 30 minutes. During the milling treatment the Mechano-Fusion machine was run with a 3 mm clearance between element and vessel wall, and with cooling water applied. The powder of composite active particles was then recovered from the drum vessel.

The experiment was repeated using the same procedure but the active particle and homogenised magnesium stearate were combined in the ratio 95:5, and milled for 60 minutes at 4,800 rpm.

This above process was repeated using the same procedure with a sample of sodium salicilate as a model drug and homogenised magnesium stearate in the ratio 90:10, where the sodium salicilate had been produced as approximately micron sized spheres by spray drying from a Buchi 191 spray dryer. It was believed that the spherical shape of these particles may be advantageous in the coating process. Milling was for 30 minutes at 4,800 rpm.

The invention claimed is:

1. Composite active particles for use in a pharmaceutical composition for pulmonary administration, each composite active particle comprising a particle of active material and magnesium stearate fused on the surface of that particle of active material, the composite active particles having a mass median aerodynamic diameter of not more than 10 μm, the magnesium stearate being applied to the particles of active material using a curved element applying high shear and compressive force.

2. Composite active particles as claimed in claim 1, which are in the form of agglomerated composite active particles.

3. Composite particles as claimed in claim 1 in which the additive particles form a coating on the surface of the particles of active material.

4. Composite active particles as claimed in claim 3 in which the coating is a discontinuous coating.

5. Composite active particles as claimed in claim 3 in which the coating is not more than 1 μm thick.

6. Composite active particles as claimed in claim 1, wherein the active material comprises one or more of: a steroid, a cromone, a β2 agonist, or a leukotriene receptor antagonist.

7. Composite active particles as claimed in claim 1, wherein the active particles comprise terbutaline, salbutamol, salmeterol, formoterol or glycopyrrolate.

8. Composite active particles as claimed in claim 1, wherein the high shear and compressive force is achieved using a gap of predetermined width.

9. Composite active particles as claimed in claim 8, wherein the gap is not more than 10 mm wide.

10. A pharmaceutical composition comprising composite active particles, each composite active particle comprising a particle of active material and magnesium stearate fused on the surface of that particle of active material, the composite active particles having a mass median aerodynamic diameter of not more than 10 μm, the magnesium stearate being applied to the particles of active material using a curved element applying high shear and compressive force.

11. A pharmaceutical composition as claimed in claim 10, which is a dry powder and is suitable for use in a dry powder inhaler.

12. A pharmaceutical composition as claimed in claim 10, which comprises a propellant and is suitable for use in a pressurized metered dose inhaler.

13. A pharmaceutical composition as claimed in claim 10, wherein the high shear and compressive force is achieved using a gap of predetermined width.

14. A pharmaceutical composition as claimed in claim 13, wherein the gap is not more than 10 mm wide.

* * * * *